United States Patent [19] [11] 4,179,462
Olivé et al. [45] Dec. 18, 1979

[54] PROCESS FOR PREPARING ACETONITRILE

[75] Inventors: Gisela Olivé; Salvador Olivé, both of Cary, N.C.

[73] Assignee: Monsanto Company, St. Louis, Mo.

[21] Appl. No.: 869,400

[22] Filed: Jan. 16, 1978

Related U.S. Application Data

[63] Continuation-in-part of Ser. No. 699,284, Jun. 24, 1976, abandoned, which is a continuation-in-part of Ser. No. 591,550, Jun. 30, 1975, abandoned.

[51] Int. Cl.² .................. C07C 120/00; C07C 121/18; C07C 121/32
[52] U.S. Cl. .............................. 260/465.1; 260/465.9; 260/585 R
[58] Field of Search .............. 260/465.1, 585 R, 465.9

[56] References Cited

U.S. PATENT DOCUMENTS

| | | | |
|---|---|---|---|
| 2,518,754 | 8/1950 | Clark | 260/583 R |
| 2,821,537 | 1/1958 | Rottig et al. | 260/585 R X |
| 3,410,904 | 11/1968 | Nozaki | 260/585 R X |
| 3,444,203 | 5/1969 | Kurtz | 260/583 R |
| 3,634,487 | 1/1972 | Khcheian et al. | 260/465.9 |
| 3,701,798 | 10/1972 | Snapp, Jr. et al. | 260/465.9 |
| 3,726,926 | 4/1973 | Brown et al. | 260/585 R |
| 3,933,888 | 1/1976 | Schlaefer | 260/465.9 |
| 4,058,548 | 11/1977 | Olive et al. | 260/465.1 |

OTHER PUBLICATIONS

C.A., 16373f, (1962), vol. 57.
C.A., 52132t, (1968), vol. 68.

*Primary Examiner*—Joseph Paul Brust
*Attorney, Agent, or Firm*—Joseph D. Kennedy; James W. Williams, Jr.

[57] ABSTRACT

A process for preparing acetonitrile by high temperature reaction of carbon monoxide, hydrogen and ammonia over a transition metal in reduced valence state as catalyst.

34 Claims, 1 Drawing Figure

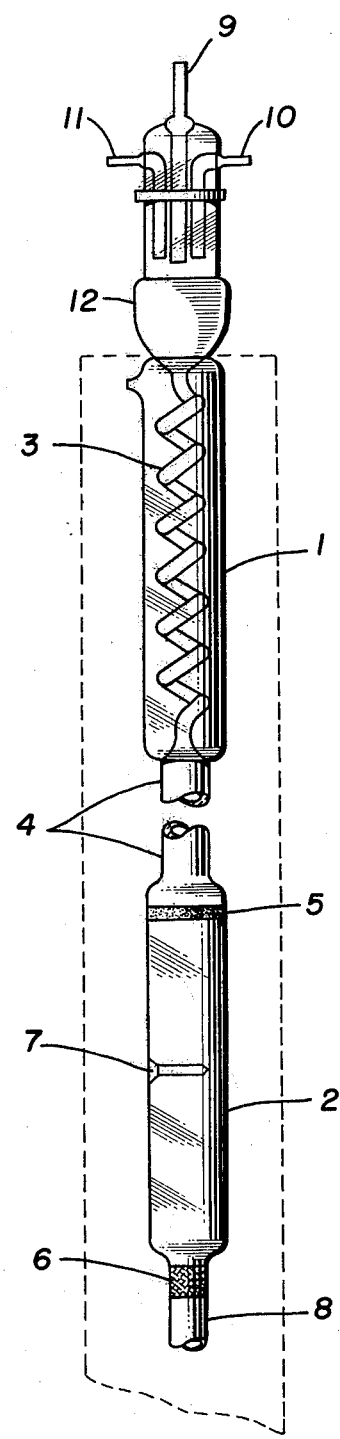

PROCESS FOR PREPARING ACETONITRILE

This application is a continuation-in-part of application Ser. No. 699,284 filed June 24, 1976, now abandoned, which is a continuation-in-part of application Ser. No. 591,550, filed June 30, 1975, now abandoned.

The present invention provides a process for preparing acetonitrile by reacting carbon monoxide, hydrogen and ammonia in the presence of a catalyst. Acetonitrile is a chemical compound which has recognized utility and considerable industrial potential. Because of its stability under a wide range of conditions it is highly appropriate as a specialty solvent able to dissolve also many inorganic salts or complexes. It is very useful as an intermediate in various syntheses. For example, it can be converted readily into many valuable products such as acids, esters, amines, aldehydes, etc. Acetonitrile can be hydrolyzed to acetamide and acetic acid. The reaction with formaldehyde leads to acrylonitrile. Such a synthesis of acrylonitrile is of particular interest in view of possible shortage of hydrocarbons, because the total synthesis of acrylonitrile using the acetonitrile produced in accordance with the herein disclosed process of invention can be accomplished with carbon monoxide, ammonia and hydrogen as sole reactants. Numerous processes for the production of acetonitrile have been reported in the technical literature. It is well known to produce acetonitrile from acetic acid or acetic anhydride and ammonia, or from ammonium acetate, or acetamide. The reaction is based on dehydration. Dehydrating agents such as $P_2O_5$, $PCl_3$, $PCl_5$, $POCl_5$, $P_2S_5$, $SOCl_2$, $AlCl_3$, $FeCl_3$, CaO, toluene sulfochloride, and the like, are used for this purpose. Dehydration is also achieved by passing acetamide vapor, or acetic acid vapor and ammonia, preferably in an air stream over refractory materials such as glass beads, alumina silica, thoria, pumice, clays, sand, alkaline earth metal phosphates, graphite, and the like, at high temperatures. Mg pyrophosphate is particularly suited for the dehydration of acetamide to acetonitrile at 350° C. (Japan. No. 71 02,651). The same is true for zinc on silica using acetic acid and ammonia at 450° C. (Hung. No. 156,577).

Acetonitrile can also be obtained from acetic acid by refluxing with urea, with aminosulfonic acid and urea, or with ClCN, or by refluxing phosphonitrile chloride $(PNCl_2)_3$ with sodium acetate or ammonium acetate, or with sodium acetate and ammonium carbonate. In the numerous syntheses where acetic acid or anhydride are involved, the purification of the acetonitrile requires a complicated procedure such as condensing the gases leaving the reactor in a water quench scrubber, feeding the quenched mixture containing about equal quantities of water to a steam stripper to remove a major part of water, passing the overhead from the stripper to a drying column to remove azeotropically with benzene the remaining water, feeding the dry acetonitrile bottoms to a distillation column to remove low-boiling impurities and passing the acetonitrile bottoms to a final stripping column, from which the pure acetonitrile (b.p. 81.3°–83.1° C.), free of ketones and water, is obtained.

Various nitrogen-containing compounds are known which have been reported to yield acetonitrile upon thermal decomposition. Examples are N-methyl formamide, sodium acetyl cyanimide, cyanacetic acid, methyl cyanoformate, lysidine hydrochloride, ethyl dichloramine, dimethylethylphenylammonium cyanide, thioacetamide, lead rhodanide and zinc acetate, diacetylmonoxime acetaldoxime, and diethyl amine.

It has also been known that thermal decomposition of ethyl amine over kaolin (700° C.), Cu (400° C.), or Ni (320°–330° C.) leads to acetonitrile (C.1918 I, 819). In general some $N_2$ ammonia, ammonium cyanide and methane are also produced. At 900° C., no acetonitrile is found, but ammonium cyanide, CO, $H_2$, $N_2$, ethylene and methane. The shorter the contact time, the more hydrocarbons are formed at this high temperature. Acetonitrile has further been obtained by heating a mixture of ethyl amine, ammonia and propylene in the presence of a Ni-$SiO_2$-catalyst (U.S. Pat. No. 2,388,218), or by conducting a stream of ethyl amine and excess oxygen over palladium supported on alumina pellets at 120° C. (U.S. Pat. No. 3,396,190).

Heretofore, a major effort in the production of acetonitrile has been directed to using hydrocarbons such as methane, ethane, ethylene, acetylene, propane, propylene, butane and isobutane as starting materials. The syntheses are based on high temperature (700°–1050° C.) reaction of the hydrocarbon and cyanogen or hydrocyanic acid, or catalytic ammoxidation.

Thus acetonitrile can be obtained by the reaction of methane with cyanogen (903° C.) or with hydrocyanic acid (916°–942° C.). Substantial amount of acrylonitrile, and with cyanogen, almost an equivalent of hydrocyanic acid are formed as by-products (U.S. Pat. Nos. 2,802,020, 3,028,413). The reaction is improved by using a catalytic amount of a free radical-generating agent, e.g. dimethyl ether, at 850° C. (U.S. Pat. No. 3,129,241).

Ethane can also be used in the place of methane in the reaction with hydrogen cyanide (655° C.) or cyanogen (600°–640° C.) in the presence of a Group VIII noble metal-containing catalyst (U.S. Pat. No. 3,057,906). It is understood that propionitrile is a by-product.

When the reaction of ethylene and HCN is carried out using oxygen and nitrogen gases (4:6:2:17) and Mo and $TiO_2$ as a catalyst at 450° C., almost equal amounts of acetonitrile and acrylonitrile are obtained (Japan, No. 68 13,202).

Similarly, with acetylene at 500°–650° C., acetonitrile and propionitrile are preponderantly formed besides a minor amount of acrylonitrile (U.S. Pat. No. 3,056,826). It has also been known to prepare acetonitrile by the reaction of methanol and excess HCN on active carbon at 320° C. (Ger. No. 464,123).

In the numerous instances where product mixtures containing acetonitrile, acrylonitrile, propionitrile, acetone, hydrocyanic acid, cyanogen etc. are present in the effluent reactor gases, these by-products pose difficult problems for the separation of pure acestonitrile requiring complicated separation steps including gas washings, simple distillation, extrative distillations and drying operations to obtain pure useful products.

Other well known processes for the production of acetonitrile from hydrocarbons, which partially have reached some technical importance, are based on the ammoxidation (oxidative ammonolysis) of hydrocarbons. Generally, a mixture of the hydrocarbon and ammonia is passed at elevated temperature over refractory materials being catalytically active or containing a catalyst. For example, acetonitrile is formed in the reactions of ammonia and the following hydrocarbons: propane, butane, isobutane, cyclohexene, or methyl cyclohexane at 500°–580° C., and ethylene or propylene at 450°–580° C., in the presence of Mo, V, or W oxides; technical propylene at 230°–430° C./-210 atm in the presence of Co-Ni-catalysts; ethylene or propylene at 600°–650° C. in the presence of activated $Al_2O_3$; gasoline fraction at 470° C. in the presence of V-Mo or Co-Mo catalysts and oxygen (5:1:5 or 6:1:5, resp.); acetylene at 440°–550° C. in the presence of molten $ZnCl_2$—NaCl or $ZnCl_2$—KCl: at 300°–500° C. in the presence of $ZnO+Al_2O_3+Cr_2O_3+NaOH$: at 400°–500° C. in the presence of $ZrO_2$: at 320°–400° C. in the presence of $ZnCl_2$, $ZnBr_2$, $ZnSO_4$ or $FeCl_3$, with addition of ZnSn silicate. ZnO or ZnS; at about 360° C. in the presence of bauxite, Al $(OH)_3$ or Fe $(OH)_3$; at 400°–420° C. in the presence of oxides of Zn, Th and Cr, also in the presence of water; at 350° C. in the presence of thorium oxide-zirconium oxide on silica; at 450° C. in the presence of zinc oxide-thorium oxide on silica; and at elevated temperatures in the presence of $ZnO+$ kaolin+activated earth (2:1:1).

Particularly suitable is an alkali or Ca salt-containing catalyst employed at 500°–600° C./2–50 mm. (Ger. No. 1,101,388).

The ammoxidation of acetylene has been promising. However, many of the stated reaction conditions are favorable to the formation of pyridine bases, higher nitriles, benzene and acetone, rendering thus the purification of acetonitrile difficult. The suppression of such side reactions requires excessively long contact times tending to tar formation. Moreover, safety problems are associated with the handling of acetylene so as to avoid explosive decomposition.

It has further been known to produce acetonitrile by the ammoxidation of acrolein, ethanol, propanol, isopropanol, acetaldehyde, acetone, ethyl formate or methyl acetate. The reaction is generally carried out in similar manner as the ammoxidation of hydrocarbons. However, the stream of the reactants generally are lead in combination with oxygen, air and/or water through the catalyst bed.

Thus, acetonitrile can be obtained from acrolein in the vapor phase using excess ammonia, air and steam at temperatures of from about 200°–350° C. in the presence of mixtures of oxides such as oxides of molybdenum, antimony, bismuth or tin, in combination with an oxide of iron, uranium, copper, vanadium, or tungsten. (U.S. Pat. No. 3,725,457).

Acetonitrile is also obtained when a mixture of the vapors of ethanol, air, ammonia and water is heated to 260°–538° C. in the presence of calcined silica-bismuth-phosphomolybdate catalyst. Acetaldehyde, acetone, propanol, isopropanol or acetic acid can similarly be converted to acetonitrile. The best yields are obtained with ethanol or acetaldehyde (Belg. No. 611,429). A catalyst containing V, Sn and P oxides on alumina, silica, Al phosphate, Bi phosphate or pumice has also been proposed for the ammoxidation of acetone, ethyl formate and methyl acetate to produce at 500°–520° C. simultaneously acetonitrile and hydrocyanic acid (Ger. No. 1,267,676).

It has further been known that acetonitrile was obtained as by-product in the preparation of anhydrous aluminum chloride at 1500°–1800° C. according to the equation $$Al_2O_3+7C+N_2+6HCl\rightarrow 2AlCl_3+3CO+2CH_3CN$$

The technical literature is silent with respect to the synthesis of acetonitrile from carbon monoxide, ammonia and hydrogen. It has been reported that the reaction of carbon monoxide with an amine such as butylamine, piperidine and aniline at elevated temperature and pressure in the liquid phase in the presence of a carbonyl-forming metal catalyst leads to carboxylic amides such as N-formylbutylamine, N-formylpiperidine and diphenylurea, respectively (Ger. No. 863,800). Ammonia apparently does not participate in this reaction.

Whereas the catalytic reaction of ammonia and carbon monoxide in the liquid phase yields urea formaldehyde resins, it has also been known that urea is formed in the gas phase in the presence of a catalyst, e.g. Pt-Group metal, at 200°–350° C. (U.S.S.R. No. 371,210).

U.S. Pat. No. 3,410,904 has unveiled that the reaction of carbon monoxide ammonia and hydrogen in the presence of Group VIII-C-Group I-B metals of atomic number from 29–79 yields trimethylamine.

More recently, it has been reported that N-alkylamines are obtained from ammonia, carbon monoxide and hydrogen at 160°–220° C., using ratios of 0.3–0.5:0-.8–1.2:1–3 mols in the presence of a catalyst comprising a combination of Group VIII, IIIA and either IA or IIA metal oxides e.g. $Fe_3O_4$-$Al_2O_3$-BaO, which have precedently been reduced and nitrided by heating with hydrogen and ammonia at 350°–500° C. (U.S. Pat. No. 3,726,926). It should be noted that the thus-obtained alkyl amines have chain lengths of 1 to 22 carbon atoms. Acetonitrile has not been observed.

The above state of the technical art shows that considerable efforts have been undertaken heretofore to produce acetonitrile by numerous various ways. All the prior methods for the manufacture of acetonitrile have in common to use hydrocarbons or derivatives thereof as raw materials.

We have now quite unexpectedly discovered an entirely novel route to the acetonitrile synthesis which provides an econimically and commercially feasible process in which inexpensive carbon monoxide, ammonia and hydrogen are brought to reaction at an elevated temperature in the presence of a metal catalyst. The present invention is generally carried out in the gaseous phase by passing a feed stream comprising carbon monoxide, hydrogen and ammonia, or only carbon monoxide and ammonia, over a catalyst containing a supported transition metal oxide, preferably molybdenum oxide or iron oxide, in a reduced state at a temperature generally in the range of from about 350° to about 550° C. and a pressure varying from subatmospheric pressures up to about 200 atmospheres, and separating the acetonitrile from the effluent product gases. As a result of this process, satisfactory yields and conversions to acetonitrile are obtained.

Under the term "transition metal" as used herein is understood any metal having partly filled d or f shells in any of their commonly occurring oxidation states.

Useful catalysts for the process of this invention preferably comprise molybdenum oxide or iron oxide which have been activated, i.e., subjected to a reductive treatment at elevated temperature. While these catalysts comprising these metal oxides, apparently in some reduced valency state exhibit different degrees of effectiveness when used per se, they generally possess additional catalytic activity when used in conjunction with well known refractory catalyst supports such as dehydrated silicic acid, i.e., dehydrated silica gel, commonly also denoted active silica; moreover, silica-alumina, silica-magnesia or zeolitic materials, commonly termed molecular sieves. But other support materials such as alumina, thoria, magnesia, pumice, bentonite, bauxite, diatomaceous earth, silicon carbide, porcelain, kaolin, asbestos, slate, and the like, may also be used and the activated metal components can be used with no support at all.

In general, the catalysts contemplated herein are prepared by a process involving the following principal steps:

(1) Providing a carrier with the desired decomposable metal salt or metal complex;
(2) subjecting said carrier at elevated temperature to oxidizing conditions, e.g., by treating with air or oxygen to convert the decomposable metal compounds into the corresponding metal oxide; and
(3) activating the resulting catalyst precursor under reducing conditions, e.g., by treating with hydrogen, carbon monoxide and/or ammonia at elevated temperature, to obtain the efficient catalyst having the metal in a reduced valency state.

However, the foregoing is illustrative and other procedures can be employed to obtain the active form of catalyst.

Under the term "decomposable transition metal compounds" as employed herein are understood those, which upon heating at 400°–600° C. are converted at least partially to the corresponding oxides by decomposition and/or replacement of their nonmetallic constituent by oxygen. Such non-metallic constituents in general are parts of a transition metal salt, such as carbonate, nitrate, carboxylate (formate, acetate, oxalate, etc.), and the like, or parts of a transition metal complex, such as carbonyl, ammonium, and the like.

Under the term "reducible transition metal compounds" as employed herein are understood those, in which upon heating at 450°–550° C. in an atmosphere containing carbon monoxide, hydrogen and/or ammonia, their metallic constituent is converted at least partially to a lower valence state and/or into a nitride and/or carbide. Such compounds are, for example, the transition metal oxides as obtained by the oxidation step described above. Higher or lower temperatures can be used for activation, e.g. about 300°–800° C.

In the case where the carrier is already provided with a metal compound which is reducible according to the procedure of step (3), the conversion to a reducible metal oxide may be omitted. The reduction may also be achived by known chemical or electrochemical methods in liquid phase.

The active component precursors can be deposited on the carrier in accordance with known standard procedures for example, by evaporating an aqueous solution containing an appropriate amount of the desired decomposable metal salt, e.g. a nitrate such as ferric nitrate, or an ammonium complex such as ammonium molybdate, jointly with a suspension or paste of the carrier material. Alternatively, a carrier may be impregnated with a relatively more concentrated solution of the active catalyst precursor and then be filtered off. In another method, a carrier precursor, e.g. sodium tetrasilicate, being dissolved in water, i.e. in the colloidal state, is precipitated or rendered insoluble by adding an acid such as chlorohydric acid, nitric acid, oxalic acid, etc. in the presence of the desired metal compound which may be dissolved or suspended. The obtained gel or co-gel is separated and/or dehydrated. Still another method is based on the precipitation by ammonia or alkali of a dissolved metal salt as a hydroxide, e.g. ferric chloride as ferric hydroxide, in the presence of a suspended carrier. The resulting carrier having finely dispersed metal hydroxide thereon is filtered off or centrifuged and dried. It is understood that the catalyst precursors used in this invention can be prepared in other ways besides those described above. Such methods are well known in the art.

The impregnated dry carriers bearing the appropriate quantity of decomposable transition metal compound are subsequently subjected to activations, i.e., to the oxidation step (2) and to the reduction step (3) as explained above. In the cases where the carrier is already provided with an appropriate metal oxide or hydrous metal oxide, e.g. FeO, $Fe_2O_3$, Fe $(OH)_2$, $MO_2O_3$, $MoO_3$, $Mo_2O_5$, etc. the oxidative pretreatment according to step (2) may be omitted. Comminuted minerals such as hematite, magnetite, taconite, molybdenite etc. after oxidation and/or reduction can also successfully be employed.

The impregnated dry catalyst precursors being preferably in the form of grains, spheres, cylinders, tablets, pellets, flakes, etc. and having convenient size are calcined, ignited, roasted or fired in an oxygen or air stream at a temperature high enough to decompose the metal compound and convert it to the corresponding metal oxide, but generally insufficient to substantially reduce the specific surface areas and the porosity as by too strong sintering or melting, although this is not necessarily objectionable. In general, the oxidation temperature is preferably within the range of 400° to 600° C., where the oxidation may be accomplished in about 1 to 10 hours, but may vary say from 300° C. to 800° C. or so. This treatment is preferably followed by a purging treatment, such as passing a stream of inert gas, e.g., nitrogen, over the catalyst precursor.

While a suitable reduction state may at times be obtained in preparation of the catalyst precursor, the catalyst precursor is ordinarily subsequently activated, conditioned and stabilized by heating under reductive conditions at a temperature sufficient to the reduction and for a time long enough to convert the metal oxide to a certain reduced state, which is considered to be the active metal species or its closest precursor. Hydrogen, carbon monoxide and/or ammonia can be used as reducing gases. For example, the activation is satisfactorily achieved by heating the pretreated carrier and catalyst in a hydrogen atmosphere at 500° C. for 3 hours. The activation with ammonia or carbon monoxide takes longer. A suitable catalyst is obtained by heating it in an $NH_3$ or CO stream at 500° C. for 15 hours. It is understood that the activation may also be carried out using a mixture of reducing gases. The activation should be longer at lower temperatures and it will also depend on the type and the quantity of catalyst to be treated, but activation temperatures can vary from say 300° C. to 800° C. or so.

Inasmuch as the catalyst precursor becomes also conditioned during the initial stages of the process, the activation operation may be dispensed with, since reducing materials such as hydrogen, carbon monoxide and ammonia or carbon monoxide and ammonia are used as the reactants. The nature of the actually active metal species has not yet been clarified and it may be that the reduced metal oxides are at least partially also hydrided and/or nitrided and/or carbided.

When after a certain operation period the catalyst may become fouled which will affect the efficiency of the catalyst to decline to a point where further operation would be uneconomical, the catalyst can be regenerated by subjecting it to oxidation and subsequent reduction as before, i.e. the steps (2) and (3) are repeated.

The best results have been obtained until now with active silica or silica gel as carrier and molybdenum as metal component under the conditions herein employed. Substantial yields of acetonitrile can also be obtained with iron, vanadium and tungsten as metal components, and somewhat lower yields with palladium, whereas ruthenium, rhodium, cobalt and nickel afford acetonitrile in lower yields at the subatmospheric or ordinary pressures which were employed. The combination of molybdenum with zinc, indium, tin or titanium does not change essentially the yield of acetonitrile while the addition of cobalt or nickel to molybdenum strongly reduces the formation of acetonitrile, but the, higher yields of methane by-product are obtained under the same operating conditions. Catalysts such as copper catalysts are frequently described for preparation of amines but catalysts other than copper and better suited for preparation of acetonitrile are in general employed herein, being transition metals and mostly found in Group VIII or the B-subgroups of Groups V, VI and VII of the Periodic Chart of the Elements.

The reactants in the present process of invention for preparing acetonitrile are carbon monoxide, ammonia and hydrogen. The feed gases may also contain an inert gas such as nitrogen as diluent, but will usually be essentially free of carbon dioxide and oxygen to avoid the complexity of additional reactive components.

The action of the metallic catalyst in the synthesis of acetonitrile according to the process of invention has not yet been clearly established. Although applicants do not wish to be bound by any specific theory and without prejudice to the present invention, there is the possibility of formation of hydrocarbon chains in a Fischer-Tropsch reaction, with the growth of the chains being interrupted by the intervention of ammonia. Ethylamine if produced can be subsequently dehydrogenated to acetonitrile under the conditions of the disclosed process. The temperatures are sufficiently high to induce facile dehydrogenation to acetonitrile. Methylamine can also be converted to acetonitrile over the catalysts at elevated temperatures. We further have found that secondary or tertiary amines never are present in the effluent gases.

The molar ratio of carbon monoxide, hydrogen and ammonia is generally in the range of from about 1:0.1–10: 0.05–4, and often 1:0.5 to 4:0.5–2. Higher contents of hydrogen in the feed gases have been found to not affect greatly the conversion of carbon monoxide to acetonitrile at atmospheric pressure, however, the selectivity to acetonitrile is substantially decreased because more methane and carbon dioxide are formed as by-products.

To enhance production of acetonitrile enough ammonia is to be used in order to obtain sufficient amination, that means, to stop the chain growth at two carbon atoms, since the formation of some propionitrile may increase with decreasing ammonia proportion. However, propionitrile is also a useful product and can be produced if desired. Any two of the reactants can be employed in the above ratios to each other, independently of the ratio to the third reactant. In carrying out this process, the feed gases may be premixed and preheated, or may be separately charged to the reaction zone which is maintained at the desired reaction temperature. The reaction zone may be made of any material which is resistant to attack by the reactants or reaction products. Refractory and corrosion-resistant materials which may be used are stainless steel, porcelain, ceramics, high-silica glass, and quartz. The reaction zone may be heated externally and/or internally by electrical means, including resistance heaters and induction heaters, or by combustion gases applied externally. The reaction zone may also be heated by combustion gases applied externally or to heating tubes extending through the reactor.

The reactor may contain a fixed, a flowing, or a fluid catalyst bed through which the reactant gas mixture is passed. The bed may also consist of a series of subsequent different sections, each containing a different catalyst and/or being operated at a different temperature. The different sections may be adapted to particular performances such as exemplified below. In order to better accomplish such divided operations the different sections each may be provided with inlets for the make-up quantities of the individual reactant gases, when necessary.

In an embodiment of the process of invention, the reactants are carbon monoxide, hydrogen and ammonia which are mixed and passed through the reactor. However, waste gases can advantageously be used. Non-hydrocarbon sources such as coal gases and furnaces gases originating from blast, carbide and phosphorus furnaces, which can if desired be freed of carbon dioxide by ordinary methods such as conversion and or washing, and of particular utility in context of the present invention, thus creating full independency from hydrocarbon sources. Carbon monoxide and/or hydrogen precursors can also suitably be used. Thus, a mixture of carbon dioxide and an excess of hydrogen can replace partially or wholly the carbon monoxide feed:

$$CO_2 + H_2 \rightleftharpoons CO + H_2O$$

It is known that methanol at elevated temperatures decomposes to carbon monoxide and hydrogen $$CH_3OH \rightleftharpoons CO + 2H_2$$

and therefore may also serve as precursor of carbon monoxide and hydrogen. The conversion or decomposition of the precursor can if desired be carried out in an appropriate first section of the reactor, and ammonia and, if necessary make-up quantities of CO and/or $H_2$ are introduced into a subsequent section providing the synthesis of acetonitrile as herein described. It is also known that ammonia is decomposed at elevated temperatures into hydrogen and nitrogen:

$$2 NH_3 \rightleftharpoons 3 H_2 + N_2$$

and hence, can also act as a hydrogen source. Under appropriate catalytic and temperature conditions, ammonia can simultaneously perform two functions in the process of invention. The decomposition of the ammonia may conveniently be conducted in a separate catalytic section of the reactor which may be at a higher temperature than the proper reaction temperature for the acetonitrile synthesis. Carbon monoxide, hydrogen and ammonia, as necessary will then be fed together with the hydrogen and nitrogen mixture, resulting from the ammonia decomposition, to the reactor.

It has been found that a molybdenum catalyst is able to produce acetonitrile, using carbon monoxide and ammonia as the sole reactants under the reaction conditions herein proposed, thus a 14% conversion of CO to acetonitrile is obtained with, for example, carbon monoxide and ammonia at a ratio of 1:4, 500° C. and atmospheric pressure. Thus carbon monoxide and ammonia can be used as the sole reactants in the present invention.

In general, the temperatures to be used in the process of the present invention vary between about 350° to 550° C. or 600° C. The upper temperature limit is governed by the temperature (about 650° to 700° C.) at which complete decomposition of the ammonia occurs. Of course, the temperature will not be so high as to cause complete decomposition of the acetonitrile product. The preferred temperature to be used in any particular operation will depend upon the nature of the feed gas mixture, the specific ratio of the reactants and the catalyst used. Higher temperatures may increase the conversion of carbon monoxide to acetonitrile per pass, but they also may decrease the selectivity and increase the formation of undesired by-products. Ordinarily the temperature will be at least sufficient to cause dehydrogenation of alkyl amines if present. Accordingly, the criteria for determining the optimum temperature to be employed in any particular case will depend on a consideration of commercial feasibility from the standpoint of striking a practical balance between conversion, selectivity and losses to by-products. It is desirable to use a temperature sufficient to give an appreciable reaction rate and significant conversion to acetonitrile, i.e. a temperature effective for the reaction.

The reactant gases in this process may be passed through the reaction zone at a gaseous hourly velocity of approximately 50 to 15,000 or more. The space velocity is herein defined as the ratio of the volume of gases at standard temperature and pressure charged per hour to the volume of the reaction space. We prefer a space velocity of about 150-200 to about 2000. The reaction, contact or stay time i.e. the period during which a unit volume of the reactants is in contact with a unit volume of catalyst accordingly may vary considerably. However, a fluidized catalyst bed in dependence of its grain size and/or bulk density should preferably be charged at the catalyst discharge limit so that a relatively small quantity of the catalyst is discharged. It is understood, that in this instance the contact time can only be modified by varying the height of the fluidized bed or by diluting the feed gas mixture appropriately with an inert gas, e.g., nitrogen. The residence time of the gas mixture in the reaction vessel containing the fluidized bed consequently is not an independent variable.

The process of the present invention proceeds well at atmospheric pressure. For example, with a catalyst containing 4.6% molybdenum (calculated as metal) on active silica, and employing a carbon monoxide, hydrogen and ammonia ratio of 1:4:2, a space velocity of 314, a temperature of 500° C. and atmospheric pressure, a conversion of carbon monoxide to acetonitrile of about 20% and a selectivity of about 45% can be reached.

In many instances, the yield and/or conversion to acetonitrile is associated with an excellent utilization of the active metal component of the catalyst. When the yield based on the metal content of the catalyst is calculated as follows $$\frac{\text{Quantity of Nitrile formed (in kg)}}{\text{Quantity of Metal (in kg)} \times \text{Time (in hr)}}$$

to define the activity of the catalyst component, for example, with a atalyst containing 0.36% iron (calculated as metal) on active silica, and employing a carbon monoxide, hydrogen and ammonia ratio of 1:4:1, a space velocity of 538, a temperature of 500° C. and atmospheric pressure, a production of 3.7 kg of acetonitrile per kg of iron per hour can be realized, and this production can be maintained for 8 hours or more.

Higher pressure appears to favor the reaction involved since the reaction products have a smaller volume than the reactants (Le Chatelier-Braum principle) and hence, the equilibrium favors nitrile formation at higher pressures. Subatmospheric pressures can be used, although presenting difficulties in recycling unconverted charge materials. Superatmospheric pressures are insofar advantageous as they permit a greater throughput of the reactants. In general a pressure within the range of 0.5 to 20 atmospheres (absolute), preferably 1 to 10 atmospheres (absolute) can be applied with atisfactory results. However, the reaction can also be conducted at higher pressures. Under consideration of a certain practical balance between CO and/or $NH_3$ conversion, overall conversion, selectivity to acetonitrile, selectivity to acetonitrile plus methane, formation of undesirable by-products such as $CO_2$ etc., such higher pressures may be employed. The use of superatmospheric pressure may accelerate production of some side products, and desired selectivity to acetonitrile, particular catalyst, temperature, etc. may at times make it desirable to employ relatively low pressures, such as not over 2 atmospheres (absolute), or only fairly modestly elevated pressures, such as not exceeding 60 to 70 atmospheres (absolute). A more broadly recited range for use is from about 0.3 to about 200 atmospheres (absolute).

The reaction effluent may be complex. It generally comprises the desired acetonitrile and uncoverted reactants (i.e., carbon monoxide, hydrogen and ammonia), methane, carbon dioxide and some nitrogen which are formed in the reaction as by-product. For the product separation, the effluent gases can, for example, be conveniently cooled to a temperature sufficiently low to condense the acetonitrile at the pressure employed. Other separation procedures can be used. Any unreacted carbon monoxide, hydrogen and ammonia may be recycled, after having been freed from carbon dioxide if desired, and admixed with make-up quantities of the reactants as necessary to obtain further quantities of acetonitrile. The carbon dioxide may be present as ammonium carbonate in the cooled off-gases and may be separated in usual manner.

EXAMPLE 1

Iron Catalyst

For the preparation of an iron catalyst according to the invention, 159.6 grams of $Fe(NO_3)_3.9\ H_2O$ are dissolved in 200 milliliters of water. To this solution are added 200 grams of active silica (E. Merck, Darmstad) in the form of grains having a diameter of about 0.2 to 0.5 millimeter (30 to 70 mesh ASTM) and the mixture is stirred for one hour. The remaining liquid is filtered and the residue dried in a rotary evaporator. The resulting catalyst precursor, after having been flushed with nitrogen, is heated under an oxygen stream at 500° C. for 8 hours. Analysis of the iron deposited on the silica gives a value of $4 \times 10^{-4}$ gram atom Fe per gram of catalyst, i.e., 2.23%. The resulting oxidized catalyst precursor is activated by heating under a hydrogen stream at 500° C. for 3 hours, or under an ammonia stream at 500° C. for 15 hours, respectively. The reduced catalyst has a bulk density of 0.54 gram/milliliter and shows ferromagnetic property.

Similarly, catalysts are prepared containing $0.64 \times 10^{-4}$ or $17.7 \times 10^{-4}$ gram atoms of iron per gram of catalyst, i.e., 0.36% or 9.88% respectively.

Molybdenum Catalyst

For the preparation of a molybdenum catalyst according to the invention, 33 grams of $(NH_4)_6Mo_7O_{24}.4H_2O$ are dissolved in 150 milliliters of water. To this solution are added 150 grams of active silica and the resulting mixture is treated as above to obtain a catalyst containing $4.8 \times 10^{-4}$ gram atoms of Mo per gram of catalyst, i.e. 4.61%.

Mixed Metal Catalyst

For the preparation of mixed metal catalysts, i.e. catalyst containing two or more different metal components on a support, an aqueous solution of two or more decomposable salts or complexes is used, or alternatively, the impregnation is repeated after the oxidation step, using a different metal salt or complex than in the first impregnation. The subsequent activation or reduction is conducted as above.

Precipitated Iron Catalyst

To a suspension of 100 grams of active silica in a solution of 730 grams of $Fe(NO_3)_3.9H_2O$ in 1.5 liters of water is added with stirring a solution of 300 grams of KOH in 1.5 liter of water. After filtering, washing and drying, the catalyst is oxidized with oxygen during 6 hours at 500° C., and then activated with $NH_3$ during 3-15 hours at 500° C.

In order to demonstrate the invention, the apparatus shown in FIGURE 1 is used.

A mixture of commercial grade carbon monoxide, hydrogen and ammonia is passed through an electrically heated Pyrex glass tube system comprising essentially two sections or compartments, namely a first section 1 being the premixer and preheater of the feed gases and a second section 2 being the reactor. An ordinary laorabory spiral cooler is used as the first section, having a jacket length of 154 mm and outside diameter of 26 mm, and a spiral tube of 3 of 10-12 windings and inside diameter of 5 mm. The preheater 1 is connected with the reactor 2 through a straight tube 4, having a length of ca 300 mm and inside diameter of 18 mm. The reactor, having a length of 150 mm and outside diameter of 26 mm. is provided at its inlet with a glass frit 5 and at the outlet with glass wool 6 to keep there between a fixed catalyst bed of 60 ml volumetric space. An inlet 7 for a thermoelement is arranged in the middle of the reactor for the temperature control. The preheater, the connection tube, the reactor and the outlet tube 8, totalizing a length of ca 800 mm are disposed in an electric furnace as shown by the dotted line.

The feed gases are introduced via rotameters and separate inlets 9, 10, 11 into the mixing chamber 12, having a volumetric capacity of 30 ml. and passes through the glass tube system, being heated to the desired temperature.

The desired temperature and gas flow ratios are adjusted. A threeway valve (not shown) on the outlet 8 allows periodic gas injections into the chromatographs. The injections are repeated every 30 minutes until constant values are obtained. Temperatures, space velocities, reactant ratios and catalysts are then varied as shown in the Tables.

Two chromatographs are used: For the acetonitrile determination a column of 183 cm length and 0.32 cm diameter, filled with "Marlophen" (Perkin-Elmer) in a F-900 Perkin-Elmer chromatograph, with FID. Operating conditions: Over 70° C.: manifold 100° C.: injector 100° C.; $N_2$ flow rate 30 ml/min. For the $CH_4$, CO and $CO_2$ determination a column of 183 cm length and 0.32 cm diameter, filled with "Poropak Q" in a GC-2 Beckman chromatograph with hot wire detection, at room temperature.

For IR and NMR analysis, the effluent is passed through chlorobenzene at $-30°$ C. The spectra show only the presence of acetonitrile. Neither hydrocarbons, $C_1$, nor methanol are detected.

Ammonia, hydrogen and water are not determined quantitatively. Since $CO_2$ reacts partly with $NH_3$ and water to form $H(NH_4)CO_3$ and remains in the pipes, the $CO_2$ content is determined as the difference:

$$CO_2 = (CO)_{feed} - (CO + CH_4 + 2AcN)_{effluent}$$

(taking into account that the formation of AcN requires 2 CO).

The term AcN herein designates acetonitrile.

The selectivity to acetonitrile is determined as the percentage of reacted CO that is found as AcN:

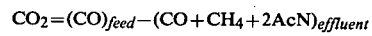

$$\text{Selectivity to AcN} = \frac{2 \text{ AcN}}{2 \text{ AcN} + CH_4 + CO_2} \times 100$$

Since, apart from an acetonitrile, also methane is considered a useful product, the selectivity to acetonitrile plus methane (AcN+$CH_4$) is given in Tables I-IV and VI.

The reactor used had a length of 150 millimeters and inside diameter of 22 millimeters. The volumetric space of the catalyst bed was about 60 milliliters and the bulk density of the supported catalyst was 0.54. The void space of the catalyst bed was about 45 milliliters. Longer reactors, i.e. longer catalyst beds, have been used as shown in Table II.

The results and particular conditions of various procedures are set forth in the accompanying Tables I through VIII.

In the work reported herein, a total material balance was not established. Indications are, for some later work, that selectivity results reported herein may be approximately halved when this is taken into account.

TABLE I

DEPENDENCE ON REACTANT RATIO
Catalyst 2.23% Fe on Silica, activated 15 hr at 500° C. with $H_2$
Reaction Temperature 500° C.

| Feed (mol/min) × 10³ | | | Conversion (%) | | Selectivity (%) | |
|---|---|---|---|---|---|---|
| CO | $H_2$ | $NH_3$ | overall | AcN | AcN | AcN + $CH_4$ |
| 2 | 1,175 | 3 | 17.0 | 5.0 | 22.0 | 28.0 |
| 2 | 2,35 | 3 | 27.0 | 6.0 | 25.0 | 34.0 |
| 2 | 3,525 | 3 | 24.0 | 6.3 | 25.0 | 46.0 |
| 2 | 4,70 | 3 | 25.0 | 8.6 | 35.0 | 65.0 |
| 2 | 5,875 | 3 | 30.0 | 7.5 | 35.0 | 65.0 |
| 2 | 7,05 | 3 | 38.0 | 9.5 | 48.0 | 70.0 |
| 2 | 8,225 | 3 | 20.0 | 9.7 | 41.5 | 75.3 |
| 2 | 4,70 | 1,5 | 33.0 | 2.7 | 12.0 | 29.0 |
| 2 | 4,70 | 6 | 30.0 | 6.2 | 25.0 | 32.0 |
| 2 | 4,70 | 9 | 17.0 | 3.0 | 20.0 | 25.0 |

The values shown are average values of several runs

TABLE II

VARIATION OF REACTOR LENGTH AND Fo CONCENTRATION

Reaction temperature 500° C.

Feed CO: $H_2:NH_3 = 2:4,7:3[(mol/min) \times 10^3]$

Catalyst Fe on Silica, activated 15 hr at 500° C. with $NH_3$

| Run | Fe (%) | Length of Reactor ($\phi$ = 22 mm) | Effluent (mol/min) $\times 10^3$ | | | | Conversion (%) | | Selectivity (%) | |
|---|---|---|---|---|---|---|---|---|---|---|
| | | | AcN | $CH_4$ | CO | $CO_2$ | overall | AcN | AcN | AcN + $CH_4$ |
| 126/3 | 2.23 | 150 mm | 0.086 | 0.175 | 1.42 | 0.233 | 29.0 | 8.6 | 29.6 | 50.8 |
| 161/2 | 2.23 | 300 mm | 0.102 | 0.134 | 1.36 | 0.30 | 32.0 | 10.2 | 32.0 | 53.0 |
| 123/1 | 2.23 | 620 mm | 0.001 | 0.101 | 1.60 | 0.137 | 20.0 | 8.1 | 40.5 | 65.7 |
| 149/1 | 0.36 | 150 mm | 0.096 | 0.076 | 1.32 | 0.412 | 34.0 | 9.6 | 28.2 | 39.4 |
| 150/1 | 9.88 | 150 mm | 0.066 | 0.110 | 1.26 | 0.50 | 37.0 | 6.6 | 17.0 | 32.6 |
| 134/4* | 2.02 | 150 mm | 0.079 | 0.099 | 1.50 | 0.243 | 25.0 | 7.9 | 31.6 | 51.4 |
| 132/1* | 2.02 | 620 mm | 0.117 | 0.061 | 1.72 | — | 14.0 | 11.7 | 79.3 | >90.0 |

*activated with $H_2$ at 415° C.

TABLE III

VARIATION OF SPACE VELOCITY

Reaction Temperature 500° C.

Catalyst Fe on Silica, activated 15 hr at 500° C. with $NH_3$

| Run | Feed (mol/min) $\times 10^3$ | | | Effluent (mol/min) $\times 10^3$ | | | | Conversion (%) | | Selectivity (%) | | Fe (%) |
|---|---|---|---|---|---|---|---|---|---|---|---|---|
| | CO | $H_2$ | $NH_3$ | AcN | $CH_4$ | CO | $CO_2$ | overall | AcN | AcN | AcN + $CH_4$ | |
| 146/2 | 1 | 2,35 | 1,5 | 0.0333 | 0.100 | 0.53 | 0.303 | 47.0 | 6.7 | 14.2 | 35.5 | |
| 4 | 2 | 4,70 | 3 | 0.090 | 0.170 | 1.11 | 0.534 | 44.5 | 9.8 | 21.8 | 40.7 | 2.23 |
| 5 | 4 | 9,4 | 6 | 0.201 | 0.292 | 2.45 | 0.856 | 36.2 | 10.0 | 27.5 | 44.8 | |
| 149/6 | 1 | 2,35 | 1,5 | 0.045 | 0.065 | 0.54 | 0.305 | 46.0 | 9.0 | 19.5 | 33.7 | |
| 2 | 2 | 4,70 | 3 | 0.096 | 0.076 | 1.32 | 0.412 | 34.0 | 9.6 | 28.2 | 39.4 | 0.36 |
| 3 | 3 | 7,05 | 4,5 | 0.167 | 0.087 | 1.85 | 0.730 | 38.3 | 11.1 | 29.0 | 36.6 | |
| 4 | 4 | 9,40 | 6 | 0.176 | 0.094 | 2.66 | 0.894 | 33.5 | 8.8 | 26.3 | 33.3 | |

TABLE IV

COMPARISION OF MOLYBDENUM AND IRON CATALYSTS

Catalysts 2.23% Fe on Silica; 4.61% Mo on Silica activated 15 hr at 500° C. with $NH_3$

| Run | Catalyst | Feed (mol/min) $\times 10^3$ | | | Effluent (mol/min) $\times 10^3$ | | | | Conversion (%) | | Selectivity (%) | |
|---|---|---|---|---|---|---|---|---|---|---|---|---|
| | | CO | $H_2$ | $NH_3$ | AcN | $CH_4$ | CO | $CO_2$ | overall | AcN | AcN | AcN + $CH_4$ |
| 155/1 | Mo | 2 | 4,7 | 3 | 0.117 | 0.172 | 1.18 | 0.414 | 41.0 | 11.7 | 28.5 | 49.5 |
| 126/3 | Fe | 2 | 4,7 | 3 | 0.086 | 0.175 | 1.42 | 0.233 | 29.0 | 8.6 | 29.6 | 59.8 |
| 155/3 | MO | 2 | 4,7 | 6 | 0.202 | 0.064 | 1.09 | 0.442 | 45.5 | 20.2 | 44.3 | 51.4 |
| 116/7 | Fe | 2 | 4,7 | 6 | 0.078 | 0.022 | 1.50 | 0.322 | 25.0 | 7.8 | 31.2 | 35.6 |

TABLE V

TEMPERATURE DEPENDENCE ON YIELD OF ACETONITRILE

Catalysts 2.23% Fe or 4.61% Mo on Silica activated 3 hr (or 15 hr, resp.) at 500° C. with $NH_3$ Feed CO:$H_2$:$NH_3$ = 2:4,7:3 [(mol/min) $\times 10^3$]

| Catalyst Metal | Temperature °C. | Conversion CO to AcN(%) | Selectivity to AcN(%) |
|---|---|---|---|
| Fe | 300 | 0.2[a] | — |
| | 400 | 0.5[b] | — |
| | 500 | 3.0 | — |
| | 600 | 0.15 | — |
| | 700 | 0.05 | — |
| Mo | 300 | 0.05 | 0.24 |
| | 400 | 12.4 | 52.8 |
| | 500 | 11.7 | 28.5 |

[a] and 0.02 propionitrile
[b] and 0.06 propionitrile

TABLE VI

COMPARISON OF ACTIVATION WITH AMMONIA AND HYDROGEN

Activation Temperature 500° C.

Catalyst 2.23% Fe on Silica

| Reductant | Time hr | Feed (mol/min) $\times 10^3$ | | | Conversion (%) | Selectivity | |
|---|---|---|---|---|---|---|---|
| | | CO | $H_2$ | n$H_3$ | | AcN | AcN + $CH_4$ |
| $NH_3$ | 3 | 2 | 3,525 | 6 | 25 | 10.0 | 10.0 |
| $NH_3$ | 3 | 2 | 4,70 | 6 | 23 | 14.2 | 10.7 |
| $NH_3$ | 3 | 2 | 5,875 | 6 | 27 | 16.0 | 23.3 |
| $NH_3$ | 15 | 2 | 3,525 | 6 | 20 | 22.0 | 25.0 |
| $NH_3$ | 15 | 2 | 4,70 | 6 | 25 | 31.2 | 35.3 |
| $NH_3$ | 15 | 2 | 5,875 | 6 | 30 | 24.7 | 33.1 |
| $H_2$ | 3 | 2 | 4,70 | 3 | 20 | 31.4 | 58.2 |
| $H_2$ | 15 | 2 | 4,70 | 3 | 20 | 32.7 | 57.8 |

TABLE VII

TRANSITION METALS OTHER THAN MOLYBDENUM AND IRON

Reaction Temperature 500° C.
Feed $CO:H_2:NH_3$ = 2:4, 7:3 [(mol/min) × $10^3$]
Activation 15 hr at 500° C. with $NH_3$
Reactortube 300 × 22 mm

| Run | Metal | Carrier | % Metal* on carrier | Conversion (%) overall | CO → AcN | Selectivity (%) AcN | AcN + CH₄ |
|-----|-------|---------|---------------------|------------------------|----------|---------------------|-----------|
| 162 | V  | SiO₂   | 1.8 | 27.5 | 2.8    | 10.2 | 11.8 |
| 158 | W  | SiO₂   | 6.5 | 31.0 | 1.2    | 3.8  | 5.0  |
| 176 | Pd | Al₂O₃ | 0.2 | 46.0 | 1.0    | 2.2  | 5.4  |
| 186 | W**| SiO₂   | 6.6 | 16.0 | 0.9    | 5.6  | 9.3  |
| 156 | Co | SiO₂   | 2.1 | 84.5 | 0.1    | 0.1  | 68.0 |
| 173 | Rh | Al₂O₃ | 0.2 | 94.0 | 0.1    | 0.1  | 50.6 |
| 159 | Zr | SiO₂   | 2.7 | —    | traces | —    | —    |
| 157 | Ru | SiO₂   | 0.2 | —    | traces | —    | —    |

*Approximate values
*Activation: 415°, H₂, 15th

TABLE VIII

BIMETALLIC CATALYSTS

Reaction Temperature 500° C.
Feed $CO:H_2:NH_3$ = 2:4,7:3[(mol/min) × $10^3$]
Activation 15 hr at 415° C. with hydrogen
Reactortube 300 × 22 mm

| Run | Metal I (weight %)ᵃ | Metal II weight %ᵃ | Carrier | Conversion (%) overall | CO → AcN | Selectivity (%) AcN | AcN + CH₄ |
|-----|---------------------|---------------------|---------|------------------------|----------|---------------------|-----------|
| 199 | Mo (3.6) | Ti (6.0)  | SiO₂   | 30.5  | 13.2 | 43.3  | 70.2 |
| 207 | Mo (3.6) | Ti (6.0)  | Al₂O₃ | 35.0  | 8.4  | 23.9  | 43.4 |
| 196 | Mo (3.6) | Zn (2.4)  | SiO₂   | 24.0  | 12.3 | 51.3  | 62.9 |
| 212 | Mo (3.6) | Cu (2.3)  | SiO₂   | 32.5  | 11.9 | 36.7  | 49.4 |
| 168ᵇ| Mo (3.6) | Fe (2.1)  | SiO₂   | 31.5  | 11.7 | 37.1  | 40.8 |
| 219 | Mo (3.8) | Na (0.4)  | SiO₂   | 34.5  | 11.2 | 32.4  | 36.8 |
| 220 | Mo (3.6) | Na (0.4)  | SiO₂   | 29.5  | 10.4 | 34.7  | 48.7 |
| 197 | Mo (3.6) | In (4.3)  | SiO₂   | 34.0  | 10.3 | 30.3  | 39.1 |
| 215ᶜ⁾| Mo (1.0)| Cr (0.6)  | SiO₂   | 28.5  | 7.6  | 26.6  | 33.0 |
| 205 | Mo (1.8) | Co (2.6)  | SiO₂   | 25.5  | 6.3  | 24.7  | 32.5 |
| 193 | Mo (3.6) | Fe (2.1)  | SiO₂   | ca 25 | 5.7  | ca 23 | ca 37 |
| 222 | Mo (3.6) | Ba (0.2)  | SiO₂   | 29.5  | 5.5  | 18.6  | 21.9 |
| 201 | Fe (1.7) | W (20.0)  | SiO₂   | 15.0  | 3.6  | 24.0  | 29.3 |
| 198 | Mo (3.6) | Sn (4.9)  | SiO₂   | 16.5  | 3.1  | 18.8  | 26.7 |
| 195 | Mo (3.6) | Co (2.2)  | SiO₂   | 45.5  | 1.5  | 3.3   | 29.2 |
| 203ᵈ⁾| Mo (3.6)| P (0.1)   | SiO₂   | 19.5  | 0.8  | 4.0   | 27.9 |
| 206 | Mo (0.6) | Bi (1.4)  | SiO₂   | 25.0  | 0.4  | 1.7   | 2.7  |
| 200 | Mo (3.6) | Ni (2.2)  | SiO₂   | 72.0  | 0.15 | 0.2   | 62.6 |

ᵃ⁾approximate values;
ᵇ⁾Activation 15 hr at 500° C. with H₂ and feed 2:8:4
ᶜ⁾Activation 15 hr at 500° C. with CO
ᵈ⁾Phosphorus instead of metal II, applied as $P_2O_5 \cdot 20MoO_3 \cdot 51H_2O$ The purpose of the present process is the production of nitriles, specifically acetonitrile. Hence various factors can be adjusted to promote the production of acetonitrile at the expense of potential concomitant products. Certain prior patents referred to herein concern the production of amines by reaction of ammonia, carbon monoxide and hydrogen. Under many of the conditions and employing catalysts described herein, no secondary or tertiary amines are produced. The prior patents at relatively low illustrative temperatures of 300° to 350° C. reported production of amines. Similarly in numerous runs conducted in the present assignee's laboratories with various catalysts, small amounts of amines have occasionally been produced, particularly in lower temperature ranges. Certain of the prior patents teach the use of high pressures, and it is known that at elevated temperatures the thermodynamic equilibrium toward amines is favored by higher pressures. However it is possible in accord with the present invention to operate under conditions which substantially eliminate amine production, as shown by the fact that amines are not observed in the effluent. Or, even if some amine is produced, it is possible to employ conditions so that amine production is minor and acetonitrile production greatly predominates over it, or at least predominates thereover. In general over a considerable range of conditions acetonitrile may be favored over amines by increasing temperature and decreasing pressure, and suitable combinations of temperature and pressure can be selected to give a desirable predominance of acetonitrile. Of course, if desired, the pressure can be fixed at atmospheric or other relatively low pressure, and sufficiently high temperatures employed to produce and to have a desired predominance of acetonitrile. Temperature limits and conditions to minimize or eliminate amine production will vary with catalysts, with some catalysts exhibiting little tendency to produce amines, but generally broad ranges of higher temperatures will be suitable for predominance of acetonitrile or having amine production substantially eliminated. As an example of a procedure producing amine along with acetonitrile, in a particular procedure employing molybdenum oxide catalyst at elevated pressure, the selectivity to methylamine at 350° C. was 2.7% compared to 22.4% to acetonitrile. At 400° C. and higher temperatures, no methyl amine was observed.

In conducting the present process it will be desirable to have a balance between factors affecting conversion and selectivity to acetonitrile. Temperatures and other conditions are desirably adjusted to achieve good reaction rates and substantial conversions. However the reaction is equilibrium limited by the law of mass action and there is generally no reason for trying to continue the reaction beyond the equilibrium value, or trying to obtain conversions beyond those which are feasible with good acetonitrile selectivity. Moreover, competing reactions may continue to use reactants after the major production of acetonitrile has occurred, and there is a tendency for selectivity to acetonitrile to drop off as certain conversion levels (based on carbon monoxide) are obtained. Temperature, pressure and time, i.e., space velocity, can be adjusted to give the desired balance between conversion and selectivity to acetonitrile, and it may be desirable to utilize fairly high space velocities. In determining the proper balance, the economics of reaction rate and conversion will be considered together with selectivity to acetonitrile. In applying these factors it may be desirable to operate near the maximum conversions attainable without a marked drop in the selectivity to acetonitrile. With some of the better catalysts the best combination of conversion (based on CO) and selectivity to acetonitrile has been found around 40% conversion, employing temperatures of about 500° C., 100 psi gauge and space velocities of about 1500 to 2500 reciprocal hours (at standard temperature and pressure). Thus in maintaining substantial selectivity to acetonitrile, e.g., at least 30, 50, 60% or more, it will usually be advantageous to stop the reaction short, possibly well short, of complete conversion as by exiting from the reaction zone.

In order to enhance production of acetonitrile, enough ammonia is used to obtain sufficient amination, and it may be advantageous to utilize at least one mole ammonia per mole carbon monoxide.

In a particular aspect, a new route from carbon monoxide, ammonia and hydrogen to acrylonitrile is considered part of the present invention. Thus the three reactants can be converted to acetonitrile by high temperature reaction, as over a transition metal catalyst as taught herein, and the acetonitrile can readily be converted to acrylonitrile by reaction with formaldehyde, as for example a vapor phase catalytic reaction of acetonitrile and formaldehyde as described, for example, in Snapp et al U.S. Pat. No. 3,701,798, employing the rare earth metal oxide catalysts there described, of the lanthanide series, or the basic metal compounds there referred to, e.g. salts or oxides of alkali metals, lead, zinc, chromium, manganese, etc. Thus, the present invention provides a new non-petroleum source and route to acrylonitrile. The finding that the three available derivatives can be reacted together over a catalyst to produce acetonitrile in substantial quantity, makes the overall route feasible and it provides an alternate and possibly advantageous source for acrylonitrile. In addition to Snapp et al, other patents illustrating procedures for converting acetonitrile to acrylonitrile are Khcheian et al, U.S. Pat. No. 3,634,487 and Schlaefer U.S. Pat. No. 3,933,888, and the disclosure of the three patents is incorporated herein by reference, particularly the illustrative procedures therein converting acetonitrile to acrylonitrile. These and other procedures known to the art can be employed for reacting acetonitrile and formaldehyde, or formaldehyde precursors or equivalents, with acetonitrile to produce acrylonitrile. Catalytic procedures are particularly appropriate, as those taking place in the vapor phase and at elevated temperatures such as 300° to 525° C. and employing various inorganic oxide or salt catalysts, for example the pyrogenic silica, Group I or II metal phosphates, or other catalysts of the aforesaid patents.

What is claimed is:

1. The process of preparing acetonitrile, by contacting carbon monoxide, hydrogen and ammonia at a temperature of at least about 350° C. and sufficiently high to induce reaction in the presence of a catalytically effective amount of catalyst comprising a transition metal in a reduced valence state which renders it effective toward the synthesis of acetonitrile, and recovering acetonitrile, said transition metal consisting essentially of transition metal other than copper, the temperature being sufficiently high at the pressure employed to cause acetonitrile production to predominate over amine production.

2. The process of preparing acetonitrile by contacting in the gas phase a feed mixture comprising carbon monoxide, hydrogen and ammonia at a sufficiently high temperature of about 350° to about 600° C. to induce reaction between said reactant gases in the presence of a catalyst containing a transition metal compound in a refractory carrier, said compound being formed by heating a reducible transition metal compound at 400°-600° C. in a reducing atmosphere containing reductants selected from the group consisting of carbon monoxide, hydrogen and ammonia or mixtures thereof for a time sufficient to reduce at least partially said transition metal compound, said transition metal consisting essentially of transition metal other than copper, the temperature being sufficiently high at the pressure employed to cause acetonitrile production to predominate over amine production, and the process being conducted under conditions with factors affecting conversion being adjusted to obtain a balance between conversion and selectivity to acetonitrile, and cooling the product mixture effluent to condense and recover acetonitrile therefrom.

3. The process of preparing acetonitrile comprising contacting carbon monoxide, hydrogen and ammonia at a sufficiently high temperature of about 350° to 550° C. to induce reaction between said reactant gases in the presence of a catalytic effective amount of a reducible compound of a transition metal supported on a porous refractory catalyst support and able to initiate and continue the acetonitrile production after having been activated by heating at a temperature of 400°-600° C. in a reducing atmosphere, selected from the group consisting of hydrogen, ammonia and carbon monoxide, for a time sufficient to reduce at least partially said metal compound, said transition metal consisting essentially of transition metal other than copper, the temperature being sufficiently high at the pressure employed to cause acetonitrile production to predominate over amine production, and the process being conducted under conditions with factors affecting conversion being adjusted to obtain a balance between conversion and selectivity to acetonitrile and stopping the reaction well short of complete conversion by having reactants leave the reaction zone, and cooling the product mixture effluent to condense and recover acetonitrile therefrom.

4. The process of claim 1 wherein the carbon monoxide, hydrogen and ammonia molar ratio is in the range of approximately 1:1–10:0.05–4.

5. The process of claim 1 wherein the carbon monoxide, hydrogen and ammonia molar ratio is in the range of 1:2–4:0.5–2.

6. The process of claim 1 wherein said transition metal is molybdenum, iron, vanadium or tungsten.

7. The process of claim 1 wherein said reactant gases are contacted at a pressure of from 0.3 to 200 atmospheres, absolute.

8. The process of claim 1 wherein said reactant gases are contacted at a pressure of from 1 to 10 atmospheres, absolute.

9. The process of claim 2 wherein said refractory carrier is silica.

10. The process of claim 2 wherein said support contains 0.1–10% of said transition metal compound, calculated as metal.

11. The process of claim 2 wherein said carrier is active silica having a specific surface area of 350–1000 square meters per gram of silica.

12. The process of preparing acetonitrile comprising contacting carbon monoxide, hydrogen and ammonia in a molar ratio of 1:0.5–4:0.5–2 at a temperature of 400°–550° C. a pressure of 1 atmosphere, absolute and a space velocity of 200–2000, in the presence of silica containing 0.1–10% of a transition metal in reduced valence state, calculated as the metal, selected from molybdenum or iron which has been activated by heating in a reducing atmosphere selected from the group consisting of hydrogen, ammonia and carbon monoxide at a temperature of about 500° C. the reaction temperature being sufficiently high at the pressure employed to cause acetonitrile production to predominate over amine production, and the process being conducted under conditions with factors affecting conversion being adjusted to obtain a balance between conversion and selectivity to acetonitrile, and cooling the product mixture effluent to condense and recover acetonitrile therefrom.

13. The process of claim 12 wherein the catalyst is obtained by impregnating said support with a decomposable molybdenum salt or iron salt which is converted to a corresponding oxide by heating at 300°–600° C. for 1–10 hours.

14. The process of claim 13 wherein said decomposable molybdenum salt is ammonium paramolybdate.

15. The process of claim 1 in which the process is conducted under conditions including temperature sufficiently high to substantially eliminate amines from the product stream.

16. The process of preparing acetonitrile and propionitrile which comprises contacting carbon monoxide, hydrogen and ammonia at a temperature of at least about 350° C. and sufficiently high to induce reaction in the presence of a catalytically effective amount of catalyst comprising the transition metal molybdenum in a reduced valence state which renders it effective toward the synthesis of nitriles and recovering nitriles.

17. The process of preparing acetonitrile by contacting carbon monoxide, hydrogen and ammonia in molar ratio of 1:0–1–10:0.5–4 at pressures of 0.3 to 200 atmospheres and at temperatures of 350° to 600° C. and sufficiently high to induce reaction in the presence of a catalyst comprising on a refractory support a transition metal in a reduced valence state which renders it effective for production of acetonitrile, said metal being from the B-subgroups of Groups V, VI and VII, of the Periodic Chart of the Elements, the temperature being sufficiently high at the pressure employed to cause acetonitrile production to predominate over amine production, and the process being conducted under conditions with factors affecting conversion being adjusted to obtain a balance between conversion and selectivity to acetonitrile.

18. The process of claim 17 in which the space velocity is about 50 to about 15,000 reciprocal hours.

19. The process of claim 17 in which the contacting is at temperatures of 400°–550° C. and pressures of 0.5 to 20 atmospheres.

20. The process of claim 17 in which a transition metal oxide has been reduced and activated by heating in the presence of a reducing atmosphere selected from hydrogen, ammonia, carbon monoxide and mixtures thereof.

21. The process of claim 20 in which the transition metal oxide has been prepared by impregnating the support with a decomposable metal salt which is converted to an oxide by heating it at 300°–800° C.

22. The process of claim 17 in which the refractory support is selected from alumina, silica, thoria and zeolites.

23. The process of claim 17 in which the heating in a reducing atmosphere is at a temperature of 400°–600° C.

24. The process of claim 2 in which the refractory carrier is alumina.

25. The process of claim 1 in which the metal is selected from the B-subgroups of Groups V, VI and VII of the Periodic Chart of the Elements, rhodium and ruthenium.

26. The process of claim 1 in which the metal is tungsten.

27. The process of claim 1 in which the metal is vanadium.

28. The process of claim 1 in which sufficient ammonia is employed to enhance production of acetonitrile, at least about 1 mole ammonia per mole of CO.

29. The process of preparing acetonitrile, by contacting carbon monoxide, hydrogen and ammonia at a temperature of at least about 350° C. and sufficiently high to induce reaction in the presence of a catalytically effective amount of catalyst comprising the transition metal molybdenum in a reduced valence state which renders it effective toward the synthesis of acetonitrile, and recovering acetonitrile.

30. The process of preparing acetonitrile by contacting carbon monoxide, hydrogen and ammonia in molar ratio of 1:0.1–10:0.05–4 at pressures of 0.3 to 200 atmospheres and at temperatures of 350° to 600° C. and sufficiently high to induce reaction in the presence of a catalyst comprising on a refractory support a transition metal in a reduced valence state which renders it effective for production of acetonitrile, said metal being molybdenum, and recovering acetonitrile from effluent product gases.

31. The process of claim 30 in which the contacting is at temperatures of 400°–550° C. and pressures of 0.5 to 20 atmospheres, a molybdenum oxide has been reduced and activated by heating in the presence of a reducing atmosphere selected from hydrogen, ammonia, carbon monoxide and mixtures thereof, the molybdenum oxide having been prepared by impregnating the support with a decomposable molybdenum salt which is converted to an oxide by heating it at 300°–800° C.

32. A process for preparing acrylonitrile by reacting carbon monoxide, hydrogen and ammonia to produce acetonitrile over a transition metal catalyst in reduced valence state effective for such reaction and at elevated temperature effective for such reaction, and reacting the acetonitrile with formaldehyde to produce acrylonitrile.

33. The process of claim 32 in which the acetonitrile is produced at temperatures of 350° to 550° C., and the acetonitrile is reacted with formaldehyde in the vapor phase at temperatures of 300° to 525° C. over an inorganic catalyst.

34. The process of claim 3 in which the transition metal is selected from molybdenum, iron, vanadium, tungsten, palladium, ruthenium, rhodium, cobalt and nickel.

* * * * *